US006482804B1

(12) United States Patent
Musunuri et al.

(10) Patent No.: US 6,482,804 B1
(45) Date of Patent: Nov. 19, 2002

(54) COMPOSITIONS AND METHODS FOR DELIVERY OF GENETIC MATERIAL

(75) Inventors: Shankar Musunuri, Downingtown; Chandrasekhar Satishchandran, Lansdale, both of PA (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 09/530,315

(22) PCT Filed: Oct. 28, 1998

(86) PCT No.: PCT/US98/22841

§ 371 (c)(1),
(2), (4) Date: Apr. 27, 2000

(87) PCT Pub. No.: WO99/21591

PCT Pub. Date: May 6, 1999

Related U.S. Application Data (60) Provisional application No. 60/063,360, filed on Oct. 28, 1997.

(51) Int. Cl.[7] .............................................. H61K 48/00
(52) U.S. Cl. ...................... 514/44; 435/320.1; 435/455; 564/47; 564/50
(58) Field of Search .................. 514/44; 435/320.1, 435/455, 458; 424/450; 564/47, 50

(56) References Cited

U.S. PATENT DOCUMENTS

| | | | |
|---|---|---|---|
| 5,580,859 A | 12/1996 | Feigner et al. ................ 514/44 |
| 5,589,466 A | 12/1996 | Feigner et al. ................ 514/44 |
| 5,593,972 A | 1/1997 | Weiner et al. ................ 514/44 |
| 5,676,954 A | 10/1997 | Brigham ...................... 424/450 |
| 5,973,117 A | * 10/1999 | Onda et al. .................. 530/350 |
| 6,110,483 A | * 8/2000 | Whitbourne et al. ....... 424/423 |
| 6,132,988 A | * 10/2000 | Sugion et al. ............. 435/69.1 |

FOREIGN PATENT DOCUMENTS

| | | |
|---|---|---|
| WO | WO 90/11092 | 3/1990 |
| WO | 91/15501 | * 10/1991 |
| WO | WO 93/17706 | 3/1993 |
| WO | WO 93/23552 | 5/1993 |
| WO | WO 94/16737 | 1/1994 |

OTHER PUBLICATIONS

Felgner et al., Enchanced Gene Delivery and Mechanism Studies with a Novel Series of Cationic Lipid Formulations, 1994, Journal of Biological Chemistry, Vol. 4, No. 4, pp. 2550–2561.*

Behr et al., Efficient gene transfer into mammalian primary endocrine cells with lipopolymine–coated DNA, Sep. 1989, Proc. Natl. Acad., vol. 86, pp. 6982–6986.*

Balasurbramaniam et al., Structural and functonal analysis of cationic transfecton lipids: the hydrophobic domain, 1996, Gene Therapy, vol. 3, pp. 163–172.*

Cruyz et al., Vaccine Delivery System, vol. 14, No. 7, pp. 667–688, 1996.*

McCluskie et al., Route of Delivery of DNA Vaccine Influence Immune Responses in Mice and Non–Human Primates, 1999, Molecular Medicine, vol. 5, pp. 287–300.*

Rhodes et al., Cationic Lipids Inhibit Intradermal Genetic Vaccination, 1994, pp. 71–75.*

Anderson, Human gene therapy, Apr. 30, 1998, vol. 392, Nature, pp. 25–30.*

Verma et al., Gene therapy–promises, problems and prospects, Sep. 18, 1997, Nature, pp. 239–242.*

Ngo et al., Computational Complexity Protein Structure Pediction, and the Levinthal Paradox, 1994, Birkhauser Boston, vol. 14, pp. 491–495.*

Chiu et al., Optimizing energy porentials for success in protein tertiary sturcture prediction, May 7, 1998, vol. 3, pp. 223–228.*

N. Ballas et al., "Liposomes Quaternary Ammonium Detergent as an Efficient Vehicle for Functional Transfer of TMV–RNA into Plant Protoplasts", *Biochim. Biophysica Acta., Biomembranes*, 939: 8–018 (1998).

J–P. Behr, "Gene Transfer with Synthetic Cationic Amphiphiles: Prospects for Gene Therapy" *Bioconjugate Chem.*, 5(5): 382–389 (Sep. 1, 1994).

J. You et al., "Surfactant–Mediated Gene Transfer for Animal Cells", *Cytotechnology*, 25:45–52 (1997).

I. Van Der Woude et al., "Novel Pyridinium Surfactants for Efficient, Nontoxic, in Vitro Gene Delivery", *Proc. Natl. Acad. Sci., USA*, 94: 1160–1165 (Feb. 1997).

T. Hara et al., "Emulsion Formulations as a Vector for Gene Delivery in Vitro and In Vivo", *Adv. Drug. Delivery Rev.*, 24(2/3):265–271 (Mar. 17, 1997).

* cited by examiner

*Primary Examiner*—Dave T. Nguyen
(74) *Attorney, Agent, or Firm*—Wyeth; Bill T. Brazil; Alan M. Gordon (57) ABSTRACT

A soluble ionic complex is formed by an aqueous mixture of a benzylammonium group-containing surfactant and a polynucleic acid sequence. When the mixture forms a vesicular complex, the sequence is packaged therein. This composition is useful in pharmaceutical compositions and in methods of delivering the polynucleic acid sequence (which preferably encodes a protein or peptide) to a cell for expression. Such methods are useful in therapy, as vaccines and as gene therapy agents.

33 Claims, 3 Drawing Sheets

COMPOSITIONS AND METHODS FOR DELIVERY OF GENETIC MATERIAL

CROSS-REFERENCE TO RELATED APPLICATIONS

This is a 371 of PCT/US98/22841, which claims the benefit of the priority of U.S. patent application Ser. No. 60/063,360, filed Oct. 28, 1997.

FIELD OF THE INVENTION

The present invention relates to compositions and methods for introducing genetic material into cells. More particularly, the present invention relates to compositions and methods for in vitro and in vivo gene transfer, which can be used to deliver protective and/or therapeutic agents including genetic material that encodes protein targets for immunization and therapeutic proteins.

BACKGROUND OF THE INVENTION

The direct introduction of a normal, functional gene into a living animal has been studied as a means for replacing defective genetic information. DNA can be introduced directly into cells of a living animal using viral vectors, liposomes, lipid complexes, ligand/DNA conjugates, and microprojectile bombardment, among other methods. Various methods and compositions for mediating transfer of DNA to cells in vivo and/or in vitro are referred to in U.S. Pat. No. 5,593,972, issued Jan. 14, 1997; U.S. Pat. No. 5,580,859, issued Dec. 3, 1996; U.S. Pat. No. 5,589,466 issued Dec. 31, 1996; U.S. Pat. No. 5,676,954, issued Nov. 19, 1996; International Patent Publications Nos. WO90/11092, published Mar. 21, 1990; WO93/17706, published Mar. 10, 1993; WO93/23552, published May 21, 1993; and WO94/16737, published Jan. 26, 1994, and the priority applications cited therein.

Despite the knowledge extant in the art, there remains a need for improved methods of DNA transfer, as well as for improved methods and compositions for in vivo and in vitro nucleic acid transfer. There remains a need for improved methods of drug delivery.

SUMMARY OF THE INVENTION

In one aspect, the invention provides soluble, ionic complex comprising an aqueous mixture of a benzylammonium group-containing surfactant and a polynucleic acid sequence. In one embodiment, the complex is a vesicular-like or liposomal-like complex comprising an aqueous mixture of a benzylammonium group-containing surfactant of the formula described herein and a polynucleic acid sequence, with the sequence substantially packaged in the vesicular complex.

In another aspect, the invention provides a mixture of multiple ionic and/or vesicular complexes of uniform size, as above described. In one embodiment, the composition is formed by mixing an aqueous solution of a benzylammonium-containing surfactant, preferably benzalkonium chloride, with a polynucleic acid sequence.

In still another aspect, the invention provides a pharmaceutical composition comprising at least one, and preferably multiple ionic complexes or vesicular complexes described above and a suitable pharmaceutical carrier.

In yet another aspect, the invention provides a method of introducing a polynucleic acid sequence into a cell comprising the step of contacting said cell with the above described complexes or compositions containing them.

In another aspect, the invention provides a method of facilitating the uptake of a polynucleic acid sequence into a cell comprising contacting the cell with a soluble ionic complex described above, or with a polynucleic acid substantially packaged in a vesicular complex formed by an aqueous mixture of a benzylammonium-containing surfactant with the polynucleic acid sequence.

In a further aspect, the invention provides methods of inducing an immune response in a mammalian or vertebrate subject to a pathogenic antigen or disease, which methods include the step of administering to cells of said subject, an effective amount of a complex as described herein, wherein the polynucleic acid sequence encodes at least one epitope that is identical or substantially similar to an epitope of a antigen of said pathogen, or a sequence encoding a target protein, said protein comprising an epitope identical or substantially similar to an epitope of a protein associated with cells that characterize said disease. The epitope or protein-encoding sequence is under the control of regulatory sequences that direct expression of said protein in the cells of said subject.

In still another aspect, the invention provides a method of treating a mammalian or vertebrate subject for a disease comprising the step of administering to cells of said subject, an effective amount of a composition comprising a complex of this invention formed by an aqueous mixture of a benzylammonium-containing surfactant and a polynucleic acid sequence, wherein said polynucleic acid sequence comprises a sequence which encodes a protein that produces a therapeutic effect on the subject or a protein that compensates for a missing, non-functional or partially functioning native mammalian protein, the protein-encoding sequence under the control of regulatory sequences that direct expression of said protein in the cells of said subject.

Other aspects and advantages of the present invention are described further in the following detailed description of the preferred embodiments thereof.

DETAILED DESCRIPTION OF THE INVENTION

The present invention provides a novel soluble ionic complex comprising an aqueous mixture of a benzylammonium group-containing surfactant; and a polynucleic acid sequence. These soluble complexes may be in the form of vesicular complexes containing polynucleic acid sequences substantially packaged therein. Compositions containing the complexes are useful as pharmaceutical (therapeutic and vaccinal) agents and as gene therapy reagents in methods for introducing the polynucleic acid sequences into a cell for a variety of therapeutic and prophylactic purposes, as well as for research purposes. The compositions and methods of the present invention provide for a high level of uptake and function of the polynucleic acid sequences and molecules.

I. The Soluble Ionic Complexes

A soluble ionic complex of this invention is formed by an aqueous mixture of a benzylammonium group-containing surfactant and a polynucleic acid sequence. The combination of the surfactant and the polynucleic acid sequence forms a vesicular-like or liposomal-like structure, in which substantially all of the polynucleic acid sequence becomes packaged. Minor amounts of the polynucleic acid sequence are associated with the exteriors of the vesicular complex. Without wishing to be bound by theory, these complexes appear to provide in vivo stability to the polynucleic acid sequences associated therewith, and thus facilitate transfection of such sequences into host cells.

A. The Surfactant

The benzylammonium group-containing surfactant is preferably a surfactant of the formula:

wherein X is an anion;

each $R^1$ is independently a hydrogen or a lower alkyl group comprising from 1 to 6 carbon atoms;

$R^2$ is $CH_2$ or —O—;

$R^3$ is H, $CH_3$, $C_2H_5$, phenyl, mono-substituted phenyl, or di-substituted phenyl, wherein said substitutions are independently selected from among $C_1$–$C_{10}$ branched or straight chain alkyls groups; and n is an integer of 2 through 7, provided that when n is 1, $R^3$ is methyl, ethyl, phenyl or substituted phenyl; when n is 4 through 6, $R^3$ is H, methyl, ethyl or phenyl; when n is 6, $R^3$ is H, methyl or ethyl; and when n is 7, $R^3$ is H or methyl.

Examples of preferred benzylammonium-group containing surfactants include those which comprise a dimethyl benzyl ammonium group linked to an alkyl group or an alkyl group linked to an aromatic group. The anion is selected from among anions that results in soluble complexes with the polynucleic acid sequence in water. In some embodiments, the anion is a halide, a sulfate, or a carbonate. In one preferred embodiment, the anion in the surfactant is a halide, such as chloride. One of skill in the art may select from among a number of suitable anions for the preparation of a surfactant suitable for the present invention.

One presently preferred example of a benzylammonium group-containing surfactant is a benzalkonium halide, such as benzalkonium chloride. Benzalkonium chloride is a cationic surfactant known to condense DNA [V. Jelen et al, *Journal of Electroanalytical Chemistry*, 377:197–203 (1994)]. It has also been used as an antimicrobial agent for parenteral preparations [*Remington's Pharmaceutical Sciences*, A. Osol, a standard reference text in this field; and "Pharmaceutical Dosage Forms: Parenteral Medication", Vol.I, K. Avis et al (eds), Marcel Dekker, Inc., New York (1992)]. Benzalkonium chloride refers to commercially available surfactants which are a mixture of alkyldimethylbenzylammonium chlorides of the formula above where $[CH_2CH_2R^2]_n$—$R^3$ is a mixture of alkyls $C_8H_{17}$ to $C_{18}H_{37}$, i.e., n is 2–6, $CH_2$ and $R^3$ is hydrogen, methyl or ethyl. Benzalkonium chloride which may be used as the surfactant in the complexes, compositions, kits and methods of the invention may be homogenous or may contain a mixture of compounds characterized by having two or more different R groups according to the formula above. Benzalkonium chloride, U.S.P. grade can be purchased from Spectrum Chemical Mfg. Corp., Gardena, Calif.

Another exemplary surfactant useful in this invention is a benzethonium halide, such as benzethonium chloride. Benzethonium chloride refers to a commercially available surfactant N,N-dimethyl-N-[2- [2-[4 (1,1,3,3-tetramethylbutylphenoxy)ethoxy]ethyl]ammonium chloride, and is described in U.S. Pat. Nos. 2,115,250, 2,170,111 and 2,229,024. It has also been used as an antimicrobial agent for parenteral preparations [Pharmaceutical Dosage Forms, cited above]. Benzethonium chloride has the formula set out above where n is 2 and $R^3$ is 4-[1,1,3,3-tetra methylbutyl]phenyl. Benzethonium chloride, U.S.P. grade can be purchased from Spectrum Chemical Mfg. Corp., Gardena, Calif.

The complexes of the present invention comprise a final concentration of benzylammonium-group containing surfactant between about 0.001 to about 2.4% by volume (w/v). Desirably, the complexes have a final concentration of the surfactant of between about 0.001–0.10% w/v. More preferably, the concentration of surfactant in the complexes is between about 0.005–0.06% w/v. A particularly desirable vesicular complex of this invention contains a benzylammonium-group containing surfactant in a concentration of between about 0.005–0.03%w/v. Manipulation of the other components of the complex, e.g., the polynucleic acid, and the buffering agents and optional isotonicity and pH adjusting agents, can reduce the toxicity of the surfactant, and permit a soluble complex to be formed at a variety of concentrations of surfactant without encountering precipitation. One of skill in the art given the instructions provided herein is expected to be able to readily manipulate the components of this invention to provide such soluble complexes at a variety of surfactant concentrations.

B. The Polynucleic Acidc Sequence

Another component of the complexes of the present invention is a polynucleic acid sequence, which when admixed with the above-described aqueous surfactant, forms a soluble ionic complex therewith. In preferred embodiments, the polynucleic acid sequence becomes substantially packaged in the vesicular-like or liposomal-like complex, and only a minor amount of such polynucleic acid sequence is associated with the exterior of the complex.

The polynucleic acid sequences which form part of the complexes of this invention are preferably "dissociated from an infectious agent", i.e., are not part of a viral, bacterial or eukaryotic vector, either active, inactivated, living or dead, that is capable of infecting a cell. In some embodiments, the polynucleic acid sequence present in compositions of the present invention are preferably free from infectious agents such as viral particles, particularly retroviral particles, and are preferably non-infectious plasmid DNA molecules. In some preferred embodiments, the compositions are free of lipids, such as cationic lipids, and/or other surfactants, and/or local anaesthetics. In some embodiments, the polynucleic acid sequences are free from the precipitating agent $CaPO_4$.

The complexes and compositions of the present invention preferably comprise between about 10 µg/ml to about 20 mg/ml of polynucleic acid sequences or molecules. Preferably, the aqueous compositions of surfactant and polynucleic acid sequences which form the complexes of the invention comprises a concentration of polynucleic acid sequences of between about 50 µg/ml to about 10 mg/ml of polynucleic acid sequences or molecules. In other preferred embodiments, the aqueous compositions of surfactant and polynucleic acid sequences which form the complexes of the invention comprises a concentration of polynucleic acid sequences of between about 100 µg/ml to about 1 mg/ml of polynucleic acid sequences or molecules.

For example, one embodiment of the complexes of the inventions contains about 0.1–5.0 mg/ml polynucleic acid in a final concentration of 0.010–0.030% w/v benzylammonium-group containing surfactant. Some preferred embodiments comprise 0.010% w/v benzylammonium-containing surfactant and 0.1 mg/ml polynucleic acid molecules. Other preferred embodiments comprise 0.010% w/v benzylammonium-group containing surfactant with about 0.5 mg/ml nucleic acid molecules. Still other preferred embodiments comprise 0.020% w/v benzylammonium-group containing surfactant with about 0.5 mg/ml nucleic acid molecules.

A particularly desirable embodiment of the complexes of the present invention is formed by between about 100–500 µg DNA molecules at a concentration of 0.1–0.5 mg/ml in a final concentration of 0.010–0.030% w/v benzalkonium chloride or benzethonium chloride. Another preferred embodiment comprises 0.010% w/v benzalkonium chloride and 0.1 mg/ml nucleic acid molecules. Still other preferred embodiments comprise 0.010% w/v benzalkonium chloride and about 0.5 mg/ml nucleic acid molecules. Some preferred embodiments comprise 0.020% w/v benzalkonium chloride and 0.5 mg/ml nucleic acid molecules. Some preferred embodiments comprise 0.010% w/v benzethonium chloride and 0.1 mg/ml nucleic acid molecules. Some preferred embodiments comprise 0.010% w/v benzethonium chloride and 0.5 mg/ml nucleic acid molecules. Some preferred embodiments comprise 0.020% w/v benzethonium chloride and 0.5 mg/ml nucleic acid molecules.

The polynucleic acid sequence of this invention may be any nucleic acid sequence and may take a variety of known forms, as taught elsewhere in the art. Thus, as used herein, the terms "polynucleic acid sequence", "nucleic acid molecule", "polynucleotide", "DNA construct", "genetic construct" and "nucleotide sequence" are interchangeable. Polynucleic acid sequences of this invention can be deoxyribonucleic acid sequences (DNA) and/or ribonucleic acid sequences (RNA). These nucleic acid sequences or molecules may be cDNA, genomic DNA, synthesized DNA, DNA molecules or plasmids or a hybrid thereof, or an RNA molecule such as mRNA. The polynucleic acid sequence may also encode antisense sequences which inhibit gene expression of genes whose expression is undesirable. A polynucleic acid molecule may serve as a template for antisense molecules and ribozymes and such sequences may be preferably linked to regulatory elements necessary for production of sufficient copies of the antisense and ribozyme molecules encoded thereby respectively or a ribozyme.

Polynucleic acid sequences or molecules useful in the present invention may serve a variety of functions, but are essentially provided to a selected host cell for a multitude of known therapeutic, prophylactic, and research uses. For example, the sequences are useful in the complexes of the invention as: 1) sequences encoding for proteins that function as prophylactic and/or therapeutic immunizing agents; 2) replacement copies of defective, missing or non-functioning genes; 3) sequences encoding therapeutic proteins; 4) antisense sequences or sequences encoding for antisense molecules; or 5) sequences encoding for, or genetic templates for, ribozymes.

Thus, in desired embodiments, the polynucleic acid sequence or molecule may comprise a sequence that encodes a peptides or protein. The sequence may be a plasmid which comprises a nucleotide sequence that encodes a protein or peptide, the encoding sequence operably linked to regulatory sequences directing expression of the protein or peptide in a host cell. Such regulatory sequences direct replication, transcription, translation and/or expression of the encoded protein or peptide in selected host cells, e.g., mammalian or vertebrate cells. As used herein, the term "expressible form" refers to polynucleic acid sequences or gene constructs which contain the necessary regulatory elements operably linked to a coding sequence that encodes a target protein, such that when present in the host cell, the coding sequence will be expressed.

The regulatory elements necessary for expression of a sequence encoding a protein or peptide include a promoter (constitutive or inducible), an initiation signal or codon, a termination signal or stop codon, and a polyadenylation signal. In addition, enhancers are often required, as well as other sequences, e.g., a Kozak region, etc. Such regulatory elements may be selected from among those known to be preferred in a selected host cell, and the polynucleic acid sequence may likewise contain codons which are known to be preferentially expressed in certain host cells. Such regulatory elements are operable in the cell of a mammalian or vertebrate subject or tissue to whom they are administered. Initiation codons and stop codon are generally considered to be part of a nucleotide sequence that encodes the desired protein. However, it is necessary that these elements are functional in the individual to whom the gene construct is administered. The initiation and termination codons must be in frame with the coding sequence.

Promoters and polyadenylation signals used must be functional within the host cells. Examples of promoters useful to practice the present invention, especially in the production of a genetic vaccine or gene therapy vector, include but are not limited to, promoters from Simian Virus 40 (SV40), Mouse Mammary Tumor Virus (MMTV) promoter, Human Immunodeficiency Virus (HIV) such as the HIV Long Terminal Repeat (LTR) promoter, Moloney virus, ALV, Cytomegalovirus (CMV) such as the CMV immediate early promoter, Epstein Barr Virus (EBV), Rous Sarcoma Virus (RSV) as well as promoters from human genes such as human actin, human myosin, human hemoglobin, human muscle creatine and human metallothionein.

Examples of polyadenylation signals useful to practice the present invention, especially in the production of a genetic vaccine for humans, include but are not limited to SV40 polyadenylation signals and LTR polyadenylation signals. In particular, the SV40 polyadenylation signal which is in pCEP4 plasmid (Invitrogen, San Diego, Calif.), referred to as the SV40 polyadenylation signal, is used.

In addition to the regulatory elements required for DNA expression, other elements may also be included in the polynucleic acid sequence of the complex. Such additional elements include enhancers, such as those selected from the group including but not limited to: human actin, human myosin, human hemoglobin, human muscle creatine and viral enhancers such as those from CMV, RSV and EBV. The polynucleic acid sequences of this invention may also include a mammalian origin of replication in order to maintain the construct extrachromosomally and produce multiple copies of the construct in a mammalian or vertebrate cell. Plasmids pCEP4 and pREP4 from Invitrogen (San Diego, Calif.) contain the Epstein Barr virus origin of replication and nuclear antigen EBNA-1 coding region which produces high copy episomal replication without integration.

Additionally, polynucleic acid sequence (e.g., DNA) which is useful to promote integration of the polynucleic acid sequence into the chromosome of the cell may also be included in the polynucleic acid sequence or DNA molecule useful in this invention. One embodiment of a polynucleic acid sequence is as a linear minichromosome including a centromere, telomeres and an origin of replication.

The polynucleic acid sequence may also contain an additional element which serves as a target for cell destruction if it is desirable to eliminate cells receiving the sequence for any reason. A herpes thymidine kinase (tk) gene in an expressible form can be included in the polynucleic acid molecule of the complex. Upon administration of the drug gangcyclovir, any cell transfected with the complex and thus producing tk, will be selectively killed. Thus, the polynucleic acid sequence can provide the means for the selective destruction of cells transfected therewith.

Depending on the use to which the complex is applied, the polynucleic acid sequence may encode a wide variety of peptides or proteins useful in pharmaceutical reagents and in research. As one example, the proteins and/or peptides encoded by the polynucleic acid sequence of the vesicular complex can include a target protein useful to induce or elicit a therapeutic or prophylactic immune response. The target protein is an immunogenic protein which shares at least an epitope with a protein from the pathogen (e.g., a virus, a bacterium, yeast, parasite, etc) or from an undesirable cell-type such as a cancer cell or a cell involved in autoimmune disease against which immunization is required. The protein can be an epitope identical or substantially similar to an epitope of a antigen of the pathogenic microorganism or undesirable cell type. As used herein, the term "substantially similar epitope" is meant to refer to an epitope that has a structure which is not identical to an epitope of a protein but nonetheless invokes a cellular or humoral immune response which cross reacts to that protein. The protein can be an epitope identical or substantially similar to an epitope of a protein associated with, e.g., hyperproliferating cells; or an epitope identical or substantially similar to an epitope of a protein associated with, e.g, cells that characterize an autoimmune disease.

The polynucleic acid sequence may also encode a therapeutic or compensating protein, i.e., it can encode a protein or peptide which can compensate for a protein product that is deficient, missing, nonfunctional or partially functioning, endogenously produced, in a cell or mammalian or vertebrate subject due to an absent, defective, non-functioning or partially functioning endogenous gene. The polynucleic acid sequence can also encode a protein or peptide that produces a therapeutic effect in a mammalian or vertebrate subject.

Exemplary protein products can readily be selected by one of skill in the art for insertion into a host cell. Among the non-exclusive lists of protein-encoding polynucleic acid sequences are sequences from an oncogene selected from the group consisting of myb, myc, fyn, ras, sarc, neu and trk. The sequences can also encode a protein product of the translocation gene bcl/abl; a protein product of P53; or for example, the protein EGRF. Still other exemplary polynucleic acid sequences useful in various aspects of this invention can encode a variable region of an antibody made by a B cell lymphoma; a variable region of a T cell surface receptor of a T cell lymphoma; a variable region of an antibody involved in B cell mediated autoimmune disease; and a variable region of a T cell surface receptor involved in T cell mediated autoimmune disease.

Thus, any polynucleic acid sequence which is desired to be inserted in a selected host cell can form part of the vesicular-like or liposomal-like complex of the present invention. One of skill in the art of therapeutics, vaccines and gene therapy may readily select and incorporate a desired polynucleic acid sequence using the teachings of the present invention.

C. The Buffer and Other Reagents in the Complex

The aqueous mixture of the benzylammonium-containing surfactant and the polynucleic acid sequence which form the soluble ionic complexes or vesicular complexes of the invention may also contain other optional agents, such as aqueous buffering agents, isotonicity adjusting agents, and pH adjusting agents. Suitable buffers for use in forming the complexes may be conventionally selected from among many known buffers used in the formation of pharmaceutical products. Among a non-exclusive list of buffers are phosphate buffers, such as phosphate buffered saline and citrate buffers. Selection of such buffers is clearly within the skill of the art. Preferably, the aqueous mixture which forms the complexes contains a buffer in a concentration of about 2 to about 50 mM, preferably about 5 to 30 mM. In one embodiment, the composition contains about 5 mM phosphate buffered saline.

The compositions of the present invention may also preferably contain isotonicity adjusting agents. For example, for pharmaceutical compositions for parenteral administration, especially intramuscularly, subcutaneously and intradermally, the aqueous mixture forming the complexes is desirably isotonic. However, as desired, one of skill in the art may readily make the compositions hypotonic or hypertonic. Some examples of-typical tonicity adjusting agents include, without limitation, sodium chloride, sucrose, mannitol, sorbitol, and trehalose. For example, where the complex is desirably hypotonic to isotonic, an tonicity adjusting agent, e.g., sucrose, is present in the aqueous admixture forming the complex in a concentration of 0 to about 9.25% w/v. For example, where the complex is desirably hypertonic, an tonicity adjusting agent, e.g., sucrose, is present in the aqueous admixture forming the complex in a concentration of greater than 9% w/v. One of skill in the art of pharmaceutical preparation can readily adjust this characteristic of the complex.

Similarly, ionic strength of the complex may be adjusted by one of skill in the art by the addition of charged molecules, such as sodium chloride. In the examples below, sodium chloride is present at a concentration of between about 0–0.9% w/v.

The aqueous mixture forming the complexes of this invention are preferably characterized by a pH between about 6.0 to about 8.0. More preferably, a desirably pH is about 6.7±0.5. Suitably pH adjustments may be readily made by a selection of agents and is well within the knowledge of one skilled in the pharmaceutical arts.

D. Examples of Complexes of the Invention

According to one embodiment of the invention, a soluble ionic complex is formed by an isotonic, aqueous admixture benzalkonium chloride and plasmid DNA, such as illustrated in Examples 1 and 4 below. In another example of the invention illustrated below, the complex of this invention is formed from an aqueous, isotonic mixture of benzethonium chloride and plasmid DNA, as illustrated in Example 5. Such compositions comprise the polynucleic acid sequence substantially packaged in the vesicular complex formed by an aqueous mixture of a benzylammonium-containing surfactant and the sequence, as demonstrated by Examples 2 and 3. Similarly, other compositions of this invention contain multiple vesicular complexes of uniform size, each vesicular complex containing polynucleic acid sequence substantially packaged in the complexes formed by admixing an aqueous mixture of the benzylammonium-containing surfactant and a solution containing the polynucleic acid sequence. The method of preparing such complexes of the invention is described in detail in Example 1 below.

The compositions of this invention, i.e., the complexes formed by the benzylammonium-group containing surfactants and polynucleic acid sequences, increase and/or facilitate uptake and/or expression of the polynucleic acid sequences by host cells, compared to the uptake or expression which occurs when the identical polynucleic acid sequence or molecule is administered to a host cell in the absence of the benzylammonium-group containing surfactants. See the results of Example 3 below.

II. Pharmaceutical Compositions of this Invention

The complexes and compositions of this invention may be employed in pharmaceutical compositions and in methods to introduce polynucleic acid sequences, e.g., genetic material, into cells in vitro or in vivo. A pharmaceutical composition of this invention comprises the soluble ionic complexes as described above in a suitable pharmaceutical carrier. In some instances, the aqueous buffer may itself be suitable. The vaccines and therapeutics according to the present invention are formulated according to the mode of administration to be used. One having ordinary skill in the art can readily formulate a pharmaceutical composition that comprises a complex as described above. In cases where intramuscular injection is the chosen mode of administration, an isotonic formulation is preferably used. Generally, additives for tonicity can include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation. The pharmaceutical preparations according to the present invention are provided sterile and pyrogen free. Although for pharmaceutical use, any route of administration may be employed, it is preferred that the composition of the invention be an injectable formulation. In one embodiment of the invention a pharmaceutical composition comprises a vesicular complex which contains the polynucleic acid molecule substantially packaged in the vesicle, with some minor amount of the sequence associated with the exterior of the vesicular complex, with the complex being in a suitable pharmaceutical carrier.

The compositions of the present invention, when used as pharmaceutical compositions, can comprise about 1 ng to about 1000 µg of DNA. In some preferred embodiments, the vaccines and therapeutics contain about 10 ng to about 800 µg DNA. In some preferred embodiments, the vaccines and therapeutics contain about 0.1 to about 500 µg DNA. In some preferred embodiments, the vaccines and therapeutics contain about 1 to about 350 µg DNA. In some preferred embodiments, the vaccines and therapeutics contain about 25 to about 250 µg DNA. In some preferred embodiments, the vaccines and therapeutics contain about 100 µg DNA.

In addition, other agents which may function as transfecting agents and/or replicating agents and/or inflammatory agents and which may be co-administered with the benzylammonium-group containing surfactants-nucleic acid molecule complexes include growth factors, cytokines and lymphokines such as alpha-interferon, gamma-interferon, platelet derived growth factor (PDGF), colony stimulating factors, such as G-CSF, GM-CSF, tumor necrosis factor (TNF), epidermal growth factor (EGF), and the interleukins, such as IL-1, IL-2, IL-4, IL-6, IL-8, IL-10 and IL-12. Further, fibroblast growth factor, surface active agents such as immune-stimulating complexes (ISCOMS), Freund's incomplete adjuvant, LPS analog including monophosphoryl Lipid A (MPL), muramyl peptides, quinone analogs and vesicular complexes such as squalene and squalene, and hyaluronic acid may also be used administered in conjunction with the compositions of the invention.

The compositions of the present invention may be combined with collagen as an emulsion and delivered parenterally. The collagen emulsion provides a means for sustained release of DNA. Preferably 50 µl to 2 ml of collagen are used. About 100 µg DNA are combined with 1 ml of collagen in a preferred embodiment using this formulation. Other sustained release formulations such as those described in *Remington's Pharmaceutical Sciences*, A. Osol, a standard reference text in this field. Such formulations include aqueous suspensions, oil solutions and suspensions, emulsions and implants as well as reservoirs and transdermal devices. In some embodiments, time release formulations for compositions of the present invention are provided. In some embodiments, it is preferred that the compositions of the present invention are time released between 6–144 hours, preferably 12–96 hours, more preferably 18–72 hours.

III. Methods of Use of the Complexes

A. In Vitro Transfection Methods

The invention provides in vitro transfection methods using the complexes and compositions comprising the aqueous mixtures of polynucleic acid sequences and benzylammonium-group containing surfactants as above described. A method of the invention facilitates the uptake of a polynucleic acid sequence into a cell comprising the step of contacting the cell with a soluble ionic complex comprising an aqueous mixture of a benzylammonium group-containing surfactant and a polynucleic acid sequence, as described above. According to this in vitro method, the complex may be introduced into tissue cultures or cells in solution in the form of a vesicular complex in which the polynucleic acid sequence is substantially packaged in the complex, with a minor amount of sequence associated with the exterior of the complex.

B. Methods of In Vivo Administration

The invention also provides in vivo therapeutic, prophylactic and gene therapy methods of transferring polynucleic acid sequences (e.g., genetic material) into cells of a mammal or a vertebrate using the pharmaceutical compositions and complexes of this invention. The benzylammonium-group containing surfactants are administered as a mixture with the nucleic acid molecule. In preferred embodiments, the benzylammonium-group containing surfactants are mixed with nucleic acid molecules to form vesicular complexes. The methods of this invention involve the step of administering to a cell or tissue of the mammal or vertebrate, a composition comprising a benzylammonium-group containing surfactant and a polynucleic acid sequence. Transfection of the polynucleic acid sequence, e.g., the DNA or RNA molecule in the surfactant:polynucleic acid sequence complex, into a living cell results in the expression of the DNA or RNA. Where the DNA or RNA encode a desired protein, the desired protein is produced. When taken up by a cell, the nucleotide sequence encoding the desired protein operably linked to the regulatory elements may remain present in the cell as a functioning extrachromosomal molecule or it may integrate into the cell's chromosomal DNA. The complex may be introduced into cells and the polynucleotide may remains as separate genetic material in the form of a plasmid. Alternatively, the complex can be employed to introduce a linear polynucleic acid sequence (DNA) into the cell, which DNA can integrate into the chromosome. When introducing the complex into the cell, reagents which promote DNA integration into chromosomes may be added.

i. Inducing Immune Responses and Therapeutic Treatment

According to some aspects of the present invention, compositions and methods are provided which prophylactically and/or therapeutically immunize an individual against a pathogen, allergen or abnormal, disease-related cell. In one embodiment, the invention provides a method of inducing an immune response in a mammalian or vertebrate subject, preferably a human, to a pathogenic antigen comprising the step of administering to cells of said subject, an effective amount of a composition or soluble complex as described above. In this complex, the polynucleic acid sequence comprises a sequence which encodes at least one epitope that is identical or substantially similar to an epitope of an antigen of the pathogen against which an immune response can be generated which will be directed against the target pathogen antigen, allergen or antigen of an abnormal and/or disease-related cell. The polynucleic acid sequence can also encode a peptide or protein which is immunologically cross reactive to the target pathogen antigen, allergen or antigen of an abnormal and/or disease-related cell. The epitope-encoding sequence, which is part of the polynucleotide sequence, is under the control of regulatory sequences that direct expression of said protein in the cells or tissue of the mammalian or vertebrate subject.

In a similar embodiment, the invention provides a method of immunizing a mammalian or vertebrate subject against a disease comprising the step of administering to said subject a composition comprising an effective amount of a composition comprising a complex of this invention, where the polynucleic acid sequence comprises a nucleotide sequence encoding a target protein, operatively linked to regulatory sequences directing the expression of said protein in the cells of said subject. The target protein can be an epitope identical or substantially similar to an epitope of a protein associated with cells that characterize the disease.

In other aspect, the method of the invention permits therapeutic treatment of a mammalian or vertebrate subject for a disease comprising the step of administering to cells of said subject, an effective amount of a composition comprising a complex described above. In the complexes useful in this aspect of the invention, the polynucleic acid sequence comprises a sequence which encodes a protein or peptide that produces a therapeutic effect on the subject, said protein-encoding sequence under the control of regulatory sequences that direct expression of said protein in the cells of said subject.

According to these aspects of the present invention, the DNA or RNA that encodes a desired protein is introduced into the cells of an individual where it is expressed, thus producing the desired protein. In such embodiments, an immune response is generated that is immunologically cross reactive with a pathogen antigen, allergen or antigen of the abnormal and/or disease-related cell. The resulting immune response is broad based: in addition to a humoral immune response, immune responses from both arms of the cellular immune response are elicited. The methods of the present invention are useful for conferring prophylactic and therapeutic immunity. Thus, a method of immunizing includes both methods of protecting an individual from pathogen challenge, or occurrence or proliferation of specific cells as well as methods of treating an individual suffering from pathogen infection, hyperproliferative disease or autoimmune disease with which the target protein is associated.

This aspect of the method of the present invention is useful to immunize individuals against pathogenic agents and organisms such that an immune response against a pathogen protein provides protective immunity against the pathogen. The present invention is useful to combat hyperproliferative diseases and disorders such as cancer by eliciting an immune response against a target protein that is specifically associated with the hyperproliferative cells. The present invention is useful to combat autoimmune diseases and disorders by eliciting an immune response against a target protein that is specifically associated with cells involved in the autoimmune condition.

In some preferred embodiments related to immunization applications, the genetic construct contains nucleotide sequences that encode a target protein and further include genes for proteins which enhance the immune response against such target proteins. Examples of such genes are those which encode cytokines and lymphokines such as those listed above in Part II. In some embodiments, it is preferred that the gene for B7.2 and/or GM-CSF is included in genetic constructs used in immunizing compositions.

The present invention may be used to immunize an individual against all pathogens such as viruses, prokaryote and pathogenic eukaryotic organisms such as unicellular pathogenic organisms and multicellular parasites. The present invention is particularly useful to immunize an individual against those pathogens which infect cells and which are not encapsulated, such as viruses, and prokaryote such as gonorrhoeae, listeria and shigella. In addition, the present invention is also useful to immunize an individual against protozoan pathogens which include a stage in the life cycle where they are intracellular pathogens. As used herein, the term "intracellular pathogen" is meant to refer to a virus or pathogenic organism that, for at least part of its reproductive or life cycle, exists within a host cell and therein produces or causes to be produced, pathogen proteins. One of skill in the art, given this disclosure can readily select viral families and genera, or pathogens including prokaryotic and eukaryotic protozoan pathogens as well as multicellular parasites, for which vaccines according to the present invention can be made. See, e.g., the tables of such pathogens in general immunology texts and in U.S. Pat. No. 5,593,972. In some preferred embodiments, the methods of immunizing an individual against a pathogen are directed against HIV, HTLV or HBV.

Because DNA and RNA are both relatively small and can be produced relatively easily, the present invention provides the additional advantage of allowing for vaccination with multiple pathogen antigens. The polynucleic acid sequence used in a composition such as a genetic vaccine employing a complex of this invention can include genetic material which encodes many pathogen antigens. For example, several viral genes may be included in a single construct thereby providing multiple targets. In addition, multiple inoculants which can be delivered to different cells in an individual can be prepared to collectively include, in some cases, a complete or, more preferably, an incomplete such as a near complete set of genes in the vaccine. For example, a complete set of viral genes may be administered using two constructs which each contain a different half of the genome which are administered at different sites. Thus, an immune response may be invoked against each antigen without the risk of an infectious virus being assembled. This allows for the introduction of more than a single antigen target and can eliminate the requirement that protective antigens be identified.

Another aspect of the present invention provides a method of conferring a broad based protective immune response against hyperproliferating cells that are characteristic in hyperproliferative diseases and to a method of treating individuals suffering from hyperproliferative diseases. In such methods, the introduction of complexes of this invention serves as an immunotherapeutic, directing and promoting the immune system of the individual to combat hyperproliferative cells that produce the target protein. As used herein, the term "hyperproliferative diseases" is meant to refer to those diseases and disorders characterized by hyperproliferation of cells. Examples of hyperproliferative diseases include all forms of cancer and psoriasis. It has been discovered that introduction of a genetic construct that includes a nucleotide sequence which encodes an immunogenic "hyperproliferating cell-associated protein" into the cells of an individual results in the production of those proteins in the vaccinated cells of an individual. As used herein, the term "hyperproliferative associated protein" is meant to refer to proteins that are associated with a hyperproliferative disease. To immunize against hyperproliferative diseases, a complex of the invention that includes a polynucleic acid sequence which encodes a protein that is associated with a hyperproliferative disease is administered to an individual.

In order for the hyperproliferative-associated protein to be an effective immunogenic target, it must be a protein that is produced exclusively or at higher levels in hyperproliferative cells as compared to normal cells. Target antigens include such proteins, fragments thereof and peptides which comprise at least an epitope found on such proteins. In some cases, a hyperproliferative-associated protein is the product of a mutation of a gene that encodes a protein. The mutated gene encodes a protein which is nearly identical to the normal protein except it has a slightly different amino acid sequence which results in a different epitope not found on the normal protein. Such target proteins include those which are proteins encoded by oncogenes such as myb, myc, fyn, and the translocation gene bcr/abl, ras, src, P53, neu, trk and EGRF.

In addition to oncogene products as target antigens, target proteins for anti-cancer treatments and protective regimens include variable regions of antibodies made by B cell lymphomas and variable regions of T cell receptors of T cell lymphomas which, in some embodiments, are also used target antigens for autoimmune disease. Other tumor-associated proteins can be used as target proteins such as proteins which are found at higher levels in tumor cells including the protein recognized by monoclonal antibody 17-1A and folate binding proteins.

While the present invention may be used to immunize an individual against one or more of several forms of cancer, the present invention is particularly useful to prophylactically immunize an individual who is predisposed to develop a particular cancer or who has had cancer and is therefore susceptible to a relapse. Developments in genetics and technology as well as epidemiology allow for the determination of probability and risk assessment for the development of cancer in individual. Using genetic screening and/or family health histories, it is possible to predict the probability a particular individual has for developing any one of several types of cancer.

Similarly, those individuals who have already developed cancer and who have been treated to remove the cancer or are otherwise in remission are particularly susceptible to relapse and reoccurrence. As part of a treatment regimen, such individuals can be immunized against the cancer that they have been diagnosed as having had in order to combat a recurrence. Thus, once it is known that an individual has had a type of cancer and is at risk of a relapse, they can be immunized in order to prepare their immune system to combat any future appearance of the cancer.

The present invention provides a method of treating individuals suffering from autoimmune diseases and disorders by conferring a broad based protective immune response against targets that are associated with autoimmunity including cell receptors and cells which produce "self"-directed antibodies. T cell mediated autoimmune diseases include Rheumatoid arthritis (RA), multiple sclerosis (MS), Sjogren's syndrome, sarcoidosis, insulin dependent diabetes mellitus (IDDM), autoimmune thyroiditis, reactive arthritis, ankylosing spondylitis, scieroderma, polymyositis, dermatomyositis, psoriasis, vasculitis, Wegener's granulomatosis, Crohn's disease and ulcerative colitis. Each of these diseases is characterized by T cell receptors that bind to endogenous antigens and initiate the inflammatory cascade associated with autoimmune diseases. Vaccination against the variable region of the T cells would elicit an immune response including CTLs to eliminate those T cells.

In RA, several specific variable regions of T cell receptors (TCRs) which are involved in the disease have been characterized. These TCRs include $V\beta$-3, $V\beta$-14, $V\alpha$-17 and $V\alpha$-17. Thus, vaccination with a DNA construct that encodes at least one of these proteins will elicit an immune response that will target T cells involved in RA [Howell, M. D et al, *Proc. Natl. Acad. Sci. USA*, 88:10921–10925 (1991); Paliard, X. et al., *Science*, 253:325–329 (1991); Williams, W. V. et al., *J. Clin. Invest.*, 90:326–333 (1992)]. In MS, several specific variable regions of TCRs which are involved in the disease have been characterized. These TCRs include $V\beta$-7 and $V\alpha$-10. Thus, vaccination with a DNA construct that encodes at least one of these proteins will elicit an immune response that will target T cells involved in MS [Wucherpfennicf, K. W., et al., *Science*, 248:1016–1019 (1990); Oksenberg, J. R., et al., *Nature*, 345:344–346 (1990)]. In scieroderma, several specific variable regions of TCRs which are involved in the disease have been characterized. These TCRs include $V\beta$-6, $V\beta$-8, $V\beta$-14 and $V\alpha$-16, $V\alpha$-3C, $V\alpha$-7, $V\alpha$-14, $V\alpha$-15, $V\alpha$-16, $V\alpha$-28 and $V\alpha$-12. Thus, vaccination with a DNA construct that encodes at least one of these proteins will elicit an immune response that will target T cells involved in scieroderma.

In order to treat patients suffering from a T cell mediated autoimmune disease, particularly those for which the variable region of the TCR has yet to be characterized, a synovial biopsy can be performed. Samples of the T cells present can be taken and the variable region of those TCRs identified using standard techniques. Genetic vaccines using the complexes of this invention can be prepared using this information.

B cell mediated autoimmune diseases include Lupus (SLE), Graves disease, myasthenia gravis, autoimmune hemolytic anemia, autoimmune thrombocytopenia, asthma, cryoglobulinemia, primary biliary sclerosis and pernicious anemia. Each of these diseases is characterized by antibodies which bind to endogenous antigens and initiate the inflammatory cascade associated with autoimmune diseases. Vaccination against the variable region of antibodies would elicit an immune response including CTLs to eliminate those B cells that produce the antibody. In order to treat patients suffering from a B cell mediated autoimmune disease, the variable region of the antibodies involved in the autoimmune activity must be identified. A biopsy can be performed and samples of the antibodies present at a site of inflammation can be taken. The variable region of those antibodies can be identified using standard techniques. Genetic vaccines can be prepared using this information. For example, in the case of SLE, one antigen is believed to be DNA. Thus, in patients to be immunized against SLE, their sera can be screened for anti-DNA antibodies and a vaccine can be prepared which includes DNA constructs that encode the variable region of such anti-DNA antibodies found in the sera.

Common structural features among the variable regions of both TCRs and antibodies are well known. The DNA sequence encoding a particular TCR or antibody can generally be found following well known methods such as those described in Kabat, et al. (1987) *Sequence of Proteins of immunological Interest* U.S. Department of Health and Human Services, Bethesda Md. In addition, a general method for cloning functional variable regions from antibodies can be found in Chaudhary, V. K., et al., *Proc. Natl. Acad. Sci. USA*, 87:1066 (1990).

In some embodiments of the invention, the individual is subject to a single vaccination to produce a full, broad immune response. In some embodiments of the invention, the individual is subject to a series of vaccinations to produce a full, broad immune response. According to some embodiments of the invention, at least two and preferably four to five injections are given over a period of time. The period of time between injections may include from 24 hours apart to two weeks or longer between injections, preferably one week apart. Alternatively, at least two and up to four separate injections are given simultaneously at different sites.

In some embodiments of the invention, a complete vaccination includes injection of a single inoculant which contains a compositions of this invention which includes a polynucleic acid sequence including sequences encoding one or more targeted epitopes.

In some embodiments of the invention, a complete vaccination includes injection of two or more different inoculants into different sites. For example, in an HIV vaccine according to the invention, the vaccine comprises two inoculants in which each one comprises compositions of this invention encoding different viral proteins. This method of vaccination allows the introduction of as much as a complete set of viral genes into the individual without the risk of assembling an infectious viral particle. Thus, an immune response against most or all of the virus can be invoked in the vaccinated individual. Injection of each inoculant is performed at different sites, preferably at a distance to ensure no cells receive both genetic constructs. As a further safety precaution, some genes may be deleted or altered to further prevent the capability of infectious viral assembly.

ii. Gene Therapy

Other aspects of the present invention relate to gene therapy; that is, to compositions for and methods of introducing nucleic acid molecules into the cells of an individual exogenous copies of genes which either correspond to defective, missing, non-functioning or partially functioning genes in the individual or which encode therapeutic proteins, i.e., proteins whose presence in the individual will eliminate a deficiency in the individual and/or whose presence will provide a therapeutic effect on the individual thereby providing a means of delivering the protein by an alternative means from protein administration. In aspects of the invention relating to gene therapy, constructs with origins of replication including the necessary antigen for activation are preferred. Thus, a method of treating a mammalian or vertebrate subject for a disease comprises administering to cells of said subject, an effective amount of a composition comprising a complex as above-described. The polynucleic acid sequence of the complex which is useful in this method comprises a sequence which encodes a protein that compensates for a missing, non-functional or partially functioning native mammalian protein, said protein-encoding sequence under the control of regulatory sequences that direct expression of said protein in the cells of said subject.

In some of the embodiments of the invention that relate to gene therapy, the gene constructs contain either compensating genes or genes that encode therapeutic proteins. Examples of compensating genes include a gene which encodes dystrophin or a functional fragment, a gene to compensate for the defective gene in patients suffering from cystic fibrosis, an insulin, a gene to compensate for the defective gene in patients suffering from ADA, and a gene encoding Factor VIII. Examples of genes encoding therapeutic proteins include genes which encodes erythropoietin, interferon, LDL receptor, GMCSF, IL-2, IL-4 and TNF. Additionally, genetic constructs which encode single chain antibody components which specifically. bind to toxic substances can be administered.

In some preferred embodiments, the dystrophin gene is provided as part of a mini-gene and used to treat individuals suffering from muscular dystrophy. In some preferred embodiments, a mini-gene which contains coding sequence for a partial dystrophin protein is provided. Dystrophin abnormalities are responsible for both the milder Becker's Muscular Dystrophy (BMD) and the severe Duchenne's Muscular Dystrophy (DMD). In BMD dystrophin is made, but it is abnormal in either size and/or amount. The patient is mild to moderately weak. In DMD no protein is made and the patient is wheelchair-bound by age 13 and usually dies by age 20. In some patients, particularly those suffering from BMD, partial dystrophin protein produced by expression of a mini-gene delivered according to the present invention can provide improved muscle function.

In some preferred embodiments, genes encoding IL-2, IL-4, interferon or TNF are delivered to tumor cells which are either present or removed and then reintroduced into an individual. In some embodiments, a gene encoding gamma interferon is administered to an individual suffering from multiple sclerosis.

Antisense molecules and ribozymes may also be delivered to the cells of an individual by introducing genetic material which acts as a template for copies of such active agents. These agents inactivate or otherwise interfere with the expression of genes that encode proteins whose presence is undesirable. Constructs which contain sequences that encode antisense molecules can be used to inhibit or prevent production of proteins within cells. Thus, production proteins such as oncogene products can be eliminated or reduced. Similarly, ribozymes can disrupt gene expression by selectively destroying messenger RNA before it is translated into protein. In some embodiments, cells are treated according to the invention using constructs that encode antisense or ribozymes as part of a therapeutic regimen which involves administration of other therapeutics and procedures. Gene constructs encoding antisense molecules and ribozymes use similar vectors as those which are used when protein production is desired except that the coding sequence does not contain a start codon to initiate translation of RNA into protein. In some embodiments, it is preferred that the vectors contain an origin of replication and an expressible form of the appropriate nuclear antigen.

Ribozymes are catalytic RNAs which are capable of self-cleavage or cleavage of another RNA molecule. Several different types of ribozymes, such as hammerhead, hairpin, Tetrahymena group I intron, ahead, and RNase P are known in the art [S. Edgington, *Biotechnology*, 10:256–262 (1992)]. Hammerhead ribozymes have a catalytic site which has been mapped to a core of less than 40 nucleotides. Several ribozymes in plant viroids and satellite RNAs share a common secondary structure and certain conserved nucleotides. Although these ribozymes naturally serve as their own substrate, the enzyme domain can be targeted to another RNA substrate through base-pairing with sequences flanking the conserved cleavage site. This ability to custom design ribozymes has allowed them to be used for sequence-specific RNA cleavage [G. Paolella et al., *EMBO J.*, 1913–1919 (1992)]. It will therefore be within the scope of one skilled in the art to use different catalytic sequences from various types of ribozymes, such as the hammerhead catalytic sequence and design them in the manner disclosed herein. Ribozymes can be designed against a variety of targets including pathogen nucleotide sequences and oncogenic sequences. Certain preferred embodiments of the invention include sufficient complementarity to specifically target the abl-bcr fusion transcript while maintaining efficiency of the cleavage reaction.

iii. Routes of Administration

In any of the above described pharmaceutical methods, the complex may be administered by any suitable route for such therapy. Among such routes are included parenteral routes, such as intramuscular, intraperitoneal, intradermal, subcutaneous, intravenous, intraarterial, intraoccular, and intrathecal routes of administration. Mucosal routes of administration are also useful, including rectal, vaginal, urethral and intranasal routes. Topical and transdermal administration is also useful for compositions and methods of this invention. Administration by inhalation is also useful. Suppository preparations or other appropriate dosage forms are also useful. Oral administration may also be employed in the methods of this invention. Preferred routes of administration include intramuscular, intraperitoneal, intradermal and subcutaneous injection.

Compositions of this invention may be administered by means including, but not limited to, traditional syringes, needleless injection devices, or "microprojectile bombardment gene guns". According to some embodiments of the present invention, the complex of this invention is simultaneously administered to an individual intradermally, subcutaneously and intramuscularly using a needleless injection device. Needleless injection devices are well known and widely available. One having ordinary skill in the art can, following the teachings herein, use needleless injection devices to deliver compositions of this invention to cells of an individual. Needleless injection devices are well suited to deliver compositions of this invention to all tissue. They are particularly useful to deliver compositions of this invention to skin and muscle cells, intradermally, subcutaneously and intramuscularly. In some embodiments, a needleless injection device may be used to propel a liquid that contains the surfactant:DNA complexes toward the surface of the individual's skin. The liquid is propelled at a sufficient velocity such that upon impact with the skin the liquid penetrates the surface of the skin, permeates the skin and muscle tissue therebeneath. In some embodiments, a needleless injection device may be used to deliver compositions of this invention to tissue of other organs in order to introduce a nucleic acid molecule to cells of that organ.

According to methods of this invention, complexes or compositions of this invention may be administered directly into the individual to be immunized. By any route, the compositions of this invention are introduced into cells which are present in the body of the individual. Delivery of the polynucleic acid sequences which encode target proteins can confer mucosal immunity in individuals immunized by a mode of administration in which the material is presented in tissues associated with mucosal immunity. Thus, in some examples, the complex of this invention is delivered by administration in the buccal cavity within the mouth of an individual, or administered rectally, vaginally, or to the urethra.

Alternatively, the compositions may be introduced by various means ex vivo into removed cells of the individual which are reimplanted after administration. Such means include, for example, ex vivo transfection, electroporation, microinjection and microprojectile bombardment. After the complex of the invention is taken up by the cells, the cells are reimplanted into the individual. It is contemplated that otherwise non-immunogenic cells that have the polynucleic acid sequences incorporated therein can be implanted into the individual even if the vaccinated cells were originally taken from another individual.

In some embodiments, the compositions of the present invention comprise as the polynucleic acid sequence an attenuated viral vaccine that may be delivered as a genetic construct. Such constructs may allow for production of viral particles. Delivery of the attenuated vaccine as a polynucleic acid sequence in a complex of this invention allows for an easier way to produce large quantities of safe, pure active immunizing product.

In some embodiments, the compositions of the present invention may be administered with or without the use microprojectiles. In some embodiments, the compositions of the present invention may be delivered to the cells of an individual free of solid particles. As used herein, the phrase "free of solid particles" is meant to refer to a liquid that does not contain any solid microprojectile used as a means to perforate, puncture or otherwise pierce the cell membrane of a cell in order to create a port of entry for compositions of this invention into the cell. For example, the compositions of the present invention are administered by means of a microprojectile particle bombardment procedure as taught by Sanford et al. in U.S. Pat. No. 4,945,050 issued Jul. 31, 1990. In some embodiments of the invention, the compositions of the present invention are administered as part of a liposome complex.

The methods of the present invention are useful in the fields of both human and veterinary medicine. Accordingly, the present invention relates to genetic immunization of mammals, and vertebrates, such as birds and fish. The methods of the present invention can be particularly useful for mammalian species including human, bovine, ovine, porcine, equine, canine and feline species.

The following examples illustrate the preferred methods for preparing the benzylammonium-containing surfactant/polynucleic acid complexes of the present invention and further illustrate that such compositions facilitate the uptake of the polynucleic acid. These examples which employ as the surfactant, benzalkonium chloride or benzethonium chloride, and as the polynucleic acid sequences, plasmid sequences containing a herpes simplex virus gD gene merely illustrate selections of the surfactant, the polynucleic acid sequence, the type of sequence and source of the sequence. It is understood by one of skill in the art, that other selections for these components of the invention may be readily selected as taught by this specification. These examples are illustrative only and do not limit the scope of the invention.

EXAMPLE 1

A Benzylammonium-Containing Surfactant/ Polynucleic Acid Formulation of The Invention A composition containing uniform ionic, vesicular complexes with polynucleic acid packaged in an aqueous benzylammonium-containing surfactant is formulated according to this invention as follows. For this example, the polynucleic acid sequence component is plasmid DNA, and the benzylammonium-containing surfactant, benzylammonium chloride. The buffer used is phosphate buffer. Other conventional buffers, such as citrate buffer, also can be used instead of phosphate buffer. Tonicity of the resulting solution may be adjusted with sodium chloride, sucrose, other conventionally known isotonic agents, such as mannitol, sorbitol, trehalose, or any non-ionic agents from the list in *Remington's Pharmaceutical Sciences*, supra.

An illustrative formulation of this invention is prepared by admixing under conditions of ambient temperature the components listed in Table I. Generally, a stock solution of the benzylammonium-containing compound is prepared in the selected buffer buffer. A polynucleic acid solution, e.g., a DNA or RNA solution is prepared containing the selected concentration of polynucleic acid sequence, e.g, plasmid DNA, in the selected buffer with the tonicity adjusting agent. Before admixture, both solutions are preferably filtered conventionally, for example, using a 0.22 μm Millex GV syringe filter. Suitable amount of the surfactant solution is added to suitable volumes of the polynucleic acid by slow mixing. The desired concentration is made by selecting the concentration of surfactant solution and a desired concentration of the polynucleic acid solution.

A composition according to this invention must be soluble. The endpoint of concentrations of the components of the complex is generally precipitation. It is preferred that the charge ratio of the benzylammonium-containing surfactant and the polynucleic acid be less than 1, and that excess positive charge be avoided. The conditions of the solution, and the amounts of polynucleic acid sequence and surfactant can be manipulated to increase solubility and reduce the toxicity of the surfactant concentrations. Desirably, the pH of the admixture is between 6 and 8, and more preferably between 6.2 and 7.2. The desired isotonicity, hypotonicity (<0.9% w/v NaCl or equivalent) or hypertonicity (>0.9% w/v NaCl or equivalent), can be adjusted by tonicity adjusting agents [see, e.g., *Remington's*, cited above].

Table I provides an illustrative composition of the invention. Other ranges of the components of the soluble ionic complex of the invention are disclosed above.

TABLE I

| Component | Range |
| --- | --- |
| Plasmid DNA | 10 μg/ml–20.0 mg/ml |
| Benzylammonium containing surfactant | 0.001–2.4% w/v |

TABLE I-continued

| Component | Range |
| --- | --- |
| Buffer (e.g. phosphate) | 2–30 mM |
| Sodium chloride | 0–0.9% w/v |
| Tonicity adjusting agent (e.g., sucrose) | 0–13% w/v |

EXAMPLE 2

Scanning and Transmission Electron Microscopic Studies with Benzalkonium Chloride:DNA Complexes Scanning electron microscopy (SEM) and transmission electron microscopy (TEM) were employed to visualize the resulting complexes formed by the benzylammonium-containing surfactant and polynucleic acid compositions of this invention.

A. Preliminary Studies

Electron microscope studies were made of the following benzalkonium chloride/DNA complex formulations of the invention:

a) 0.025% benzalkonium chloride/0.5 mg/mL of DNA,
b) 0.0125% benzalkonium chloride/0.5 mg/mL DNA,
c) 0.025% benzalkonium chloride/0.1 mg/mL of DNA,
d) 0.012% benzalkonium chloride/0.05 mg/mL of DNA.
  These formulations were made in the same manner as described for Example 1, except that the benzalkonium chloride concentrations are different as stated above. Each formulation containing 8.71% sucrose w/v and 5 mM phosphate buffer at pH6.7±0.5.

Electron microscopic photographs (not pictured) illustrated that each formulation formed uniform vesicular complexes indistinguishable from those derived from classical liposomes and cationic liposomes.

B. Additional SEM and TEM Studies i. Formulations of this invention were prepared by mixing DNA at 0.5 mg/mL, with benzalkonium chloride (0.02% w/v) in 10 mM citrate or phosphate buffers, pH 6.7 (±0.5), and 50 mM NaCl, substantially as described above.

The structures visible by both SEM and TEM are indistinguishable from those derived from classical liposomes and cationic liposomes. The size of these particles varied from 50 nm to 230 nm. However, most structures had an uniform size distribution ranging from 70 to 100 nm.

ii. Additional studies were performed by mixing DNA at 5 mg/ml in higher concentrations of benzalkonium chloride, up to 0.04% w/v, in 10 mM citrate or phosphate buffers, pH 6.7 (±0.5), and 50 mM NaCl, substantially as described above. Benzalkonium chloride alone does not form vesicular complexes in water. At higher than ≧0.1% w/v, benzalkonium chloride alone is soluble and forms micelles. However, upon addition of DNA, vesicular complexes are formed, when observed by SEM. The vesicular complexes range in size from 50 (at 0.01% benzalkonium chloride) to 400 nm particles (0.04% w/v benzalkonium chloride). Benzalkonium chloride at concentrations higher than ≧0.04% w/v under these conditions, in the presence of DNA formed a fine precipitate that contained DNA (determined by agarose gel electrophoresis of the precipitate). At concentrations above 0.04% benzalkonium chloride under these conditions, the precipitates were snowy and flocculent.

These observations and the SEM and TEM pictures described herein (not pictured) show that benzalkonium chloride:DNA compositions according to this invention form a vesicular-like or liposomal-like structure. The quaternary ammonium cationic head group of the benzalkonium chloride is positively charged independent of protonation, and forms complexes with DNA, that decrease its solubility. At benzalkonium chloride concentrations lower than 0.04% w/v in the compositions above, the complexes remain soluble, while at benzalkonium chloride concentrations ≧0.04% w/v in the compositions above, the hydrophilicity of these complexes is reduced to near neutrality. The association of DNA with the precipitates further indicates complexation.

iii. SEM was carried out on formulations that contained two different concentrations of DNA (100 μg/ml and 0.5 mg/ml), and fixed concentrations of benzalkonium chloride (0.02% w/v). Similar particle distribution was found at both concentrations of DNA, but in larger numbers with higher DNA concentrations. Larger particles in higher DNA concentrations appear to have derived from the fusion of several 50 nm particles. Formation of larger particles was dependent on the concentration of DNA in the formulation. These particles were visualized by shadow casting in SEM analysis using carbon, and were visible by short (10 second) exposure to the contrasting agent uranyl acetate in TEM analysis. The TEMs show membranous structures typical of liposomes described in literature.

As controls, SEM of DNA alone and benzalkonium chloride alone in aqueous solutions were performed. Vesicular structures are found only when aqueous solutions of DNA and benzalkonium chloride are mixed. TEMs show structures that are vesicular and some are multilamellar. Membranous structures found in these TEMs are consistent with the formation of lamellar vesicular complexes in liposomes. These results show that benzalkonium chloride:DNA complexes form lamellar and vesicular structures, similar to those described for liposomes and liposomal formulations.

EXAMPLE 3

Labeled DNA is Associated with the Vesicular complexes, SEM and TEM Analysis

A. Preparation of Open Circular Plasmid DNA.

Supercoiled (SC) plasmid DNA was converted into an open-circular form by heating at 80° C., for 4 hours. Nearly 80% of SC DNA was converted to nicked open circular (OC) fonn by this method. The amount of DNA converted to OC was quantified using a video gel-scanner, following electrophoretic separation of SC and OC forms. The OC was purified to nearly 95% purity on a Q-Sepharose matrix using a NaCl step gradient.

B. Preparation of Bioltinylated dUTP DNA.

Fifty micrograms of nicked OC DNA was subjected to a strand displacement reaction using Klenow (the non-proofreading proteolytic fragment of DNA polymerase of *E. coli*), and dNTP. The dNTP mixture contained dATP, dGTP, dCTP, dUTP, and Bio-dUTP. Bio-dUTP has biotin on an 11 carbon linker attached to the base uracil. The nucleotide concentration was at 50 μM, while the bio-dUTP was at 2 μm, and dUTP was at 20 μM. The plasmid was purified from free nucleotides by two rounds of ethanol precipitation, and two 70% ethanol washes. The amount of biotin incorporated into the plasmid was determined by a kinetic ELISA, by reacting dilutions of the plasmid with streptavidin-horseradish peroxidase (HRP). Three molecules of biotin were incorporated per plasmid molecule.

C. Preparation of Streptavidin-Colloidal Gold Conjugated Plasmid DNA.

One microgram of a 5 Kbp plasmid DNA corresponds to $1.25 \times 10^{14}$ molecules ($3.75 \times 10^{13}$ biotin). Five hundred micrograms of mixture in one milliliter was reacted with $10^{11}$ molecules of gold-conjugated streptavidin. This ensures absence of free streptavidin-gold conjugates [T. Daemen et al, *Hepatology*, 26:416 (1997)]. Benzalkonium chloride at 0.02% was added to the mixture to form complexes. The mixture was analyzed by TEM.

D. TEM Analysis

TEM analysis of the above-prepared gold labeled DNA in the benzylammonium-containing surfactant/polynucleic acid sequence compositions of this invention demonstrated that the gold-labeled DNA is found in structures (complexes) that are identical to those found by carbon shadowing. These structures show that DNA is within the vesicular membranes. Vesicular complexes in some fields appear to be multilamellar, and the gold labeled plasmid molecules are interspersed within these lamellae. Electron diffraction shows densities corresponding to gold that were detected on these membranes, and within membranes. This analysis demonstrates that benzalkonium chloride:DNA complexes form vesicular complexes, and the DNA is in the vesicular space, intimately associated with the membrane.

EXAMPLE 4

Enhancement of DNA Uptake Using Compositions of the Invention

A. The Formulations Tested

Four different formulations were prepared to evaluate the ability of aqueous mixtures of benzylammonium-containing surfactants and polynucleic acid sequences to facilitate DNA delivery. The four formulations of the invention and the control are reported in Table 2 below.

Formulation 1 (2 mL formulation) was prepared as follows: 0.5% benzalkonium chloride stock was prepared in 5 mM phosphate buffer. A DNA plasmid was constructed which contained the Herpes Simplex Virus gene encoding the $gD_2$ protein linked to a cytomegalovirus promoter and SV40 polyadenylation site. This plasmid, referred to as plasmid 24, is described in detail in International Patent Publication No. WO97/41892, published Nov. 13, 1997. The DNA plasmid solution was prepared containing 0.5 mg/mL plasmid DNA in 5 mM phosphate buffer with 8.71% sucrose. Both the benzalkonium chloride stock solution and DNA solution were filtered using 0.22 μm Millex GV syringe filter. Forty μL of benzalkonium chloride stock solution was added to 1.96 mL of DNA solution (0.5 mg/mL) by slow mixing.

Formulation 2 (2 mL formulation) was prepared as follows: 0.5% benzalkonium chloride stock was prepared in 5 mM phosphate buffer. DNA solution contain the above-described plasmid 24 (0.5 mg/mL) was prepared in 5 mM phosphate buffer with 8.71% sucrose. Both the benzalkonium chloride stock solution and DNA solution were filtered using 0.22 μm Millex GV syringe filter. Eighty μL of benzalkonium chloride stock solution was added to 1.92 mL of DNA solution (0.5 mg/mL) by slow mixing.

Formulation 3 (2 mL formulation) was prepared as follows: 0.5% benzalkonium chloride stock was prepared in 5 mM phosphate buffer. DNA solution containing the above-described plasmid 24 (0.5 mg/mL) was prepared in buffer solution containing 5 mM phosphate and 150 mM of sodium chloride. Both the benzalkonium chloride stock solution and DNA solution were filtered using 0.22 μm Millex GV syringe filter. One hundred twenty μL of benzalkonium chloride stock solution was added to 1.88 mL of DNA solution (0.5 mg/mL) by slow mixing.

As a positive control, a DNA only formulation was prepared containing 0.5 mg/mL DNA of plasmid 24 in 30 mM citrate buffer, 0.1% ethylenediamine tetraacetic acid (EDTA), 150 mM NaCl at pH 6.7±0.5. As a negative control, a DNA only formulation was prepared containing 0.5 mg/ml DNA of plasmid 23 (no HSV insert) in 30 mM citrate buffer, 0.1% EDTA, 150 mM NaCl at pH 6.7±0.5.

TABLE 2

| Components | Formulations | | |
|---|---|---|---|
|  | 1 | 2 | 3 |
| Plasmid DNA (mg/mL) | 0.5 | 0.5 | 0.5 |
| Benzalkonium chloride (w/v) | 0.01% | 0.02% | 0.06% |
| Sucrose (w/v) | 8.71% | 8.71% | 0 |
| Sodium Chloride (mM) | 0 | 0 | 150 |
| Phosphate buffer (mM) | 5 | 5 | 5 |
| pH | 6.7 ± 0.5 | 6.7 ± 0.5 | 6.7 ± 0.5 |

B. Protocol of Test

Six groups of BALB/c mice (5 mice/group) were immunized intramuscularly with 50 µg plasmid DNA in a total volume of 100 µL per dose, which was distributed between 3–4 sites per leg on Day 1. The plasmid was administered in compositions with different concentrations of benzalkonium chloride as follows:

Group I received Formulation 1 (50 µg plasmid in 0.01% benzalkonium chloride). Group II received Formulation 2 (50 µg plasmid in 0.02% benzalkonium chloride). Group III received Formulation 3 (50 µg plasmid in 0.06% benzalkonium chloride). Group IV received positive control (50 µg plasmid 24 without any transfection facilitating agent); and Group V received negative control (plasmid 23 with no HSV insert and without any transfection facilitating agent).

Serum was collected prior to first injection (Day 0) and at two weeks post injection (Day 14). Animals were boosted once more at the same dosage at four weeks (Day 28). After the final injection an additional serum sample was taken. Two weeks following the final immunization (Day 42), mice were euthanized using halothane, followed by cervical dislocation and the spleens were harvested.

C. In Vivo Results

Figure 1:
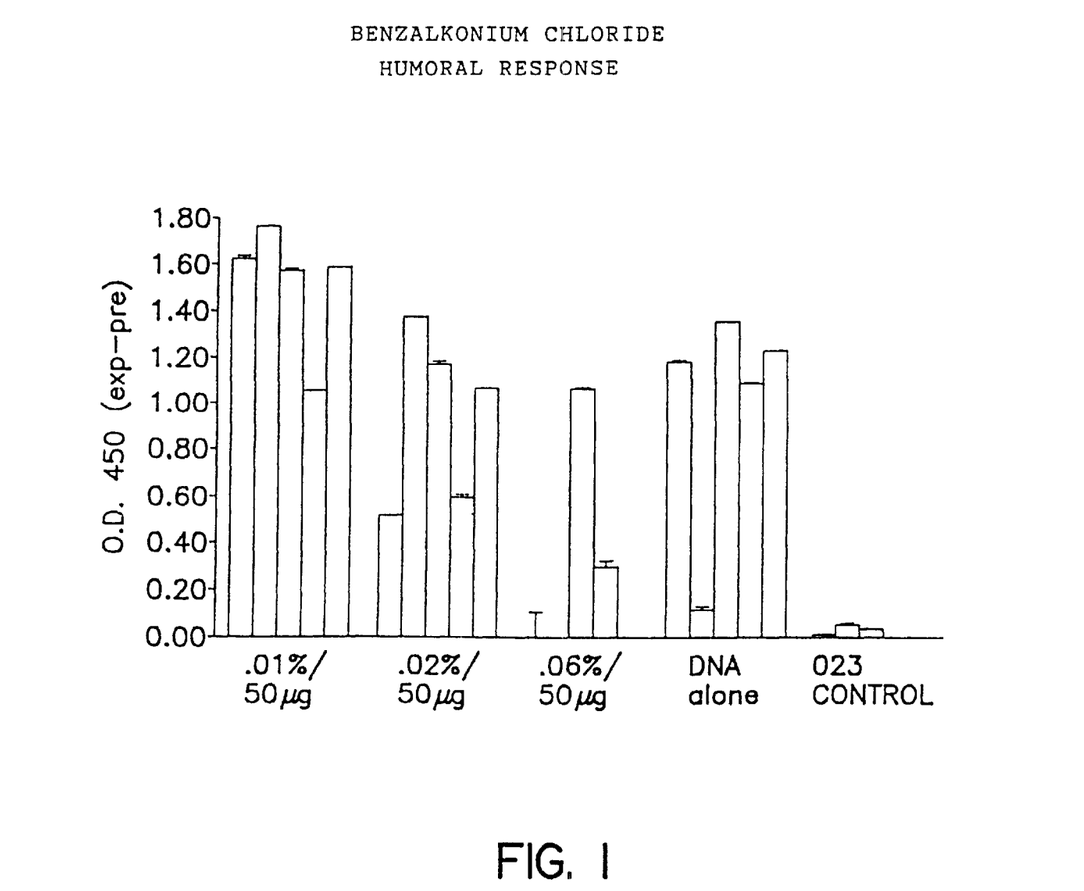
FIG. 1 is a bar graph showing the humoral (antibody) response measured in optical density (OD) at 450 nm in serum of individual Balb/C mice to an aqueous composition of the invention containing the indicated concentrations of benzalkonium chloride and indicated amounts of a DNA plasmid encoding the $gD_2$ protein of Herpes Simplex Virus as measured by standard ELISA. The positive and negative controls are the same plasmid with no transfection facilitating agent (DNA only) and the plasmid with no $gD_2$ encoding sequence with no transfection facilitating agent (O23ctrl). Each bar represents a single animal. See Example 4 below.
Figure 2:
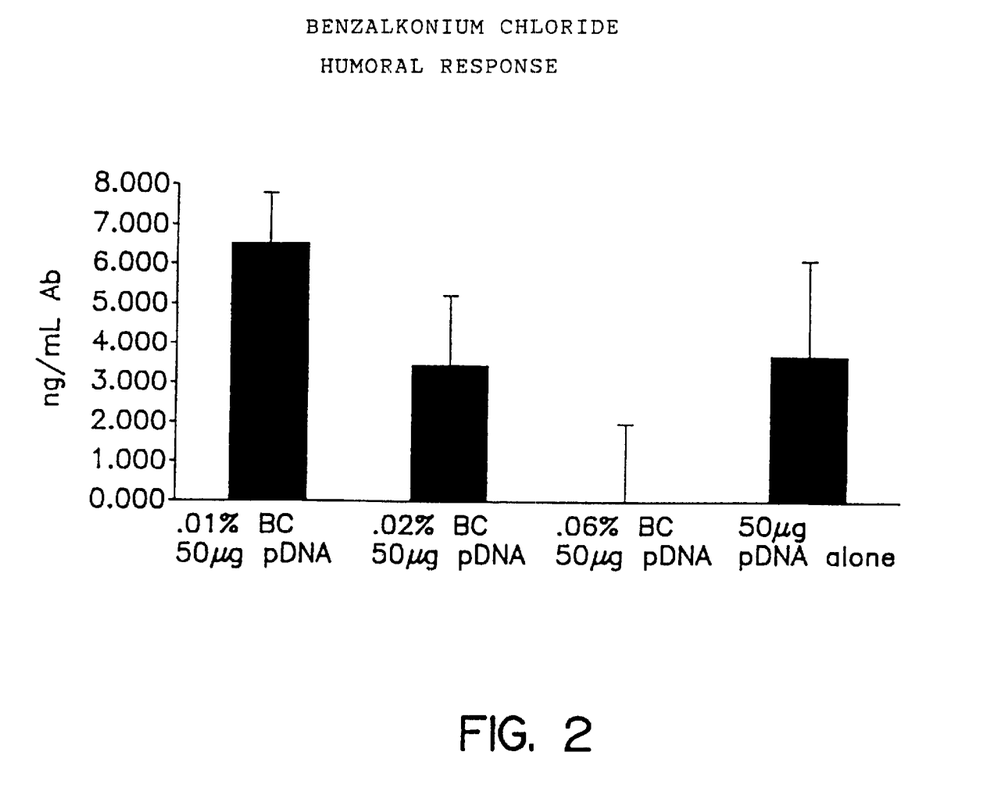
FIG. 2 is a bar graph showing group average humoral (antibody) responses in the animals of FIG. 1. The responses are measured according to Antibody Response Calculations in ng/ml, as defined in Example 4 below.
Figure 3:
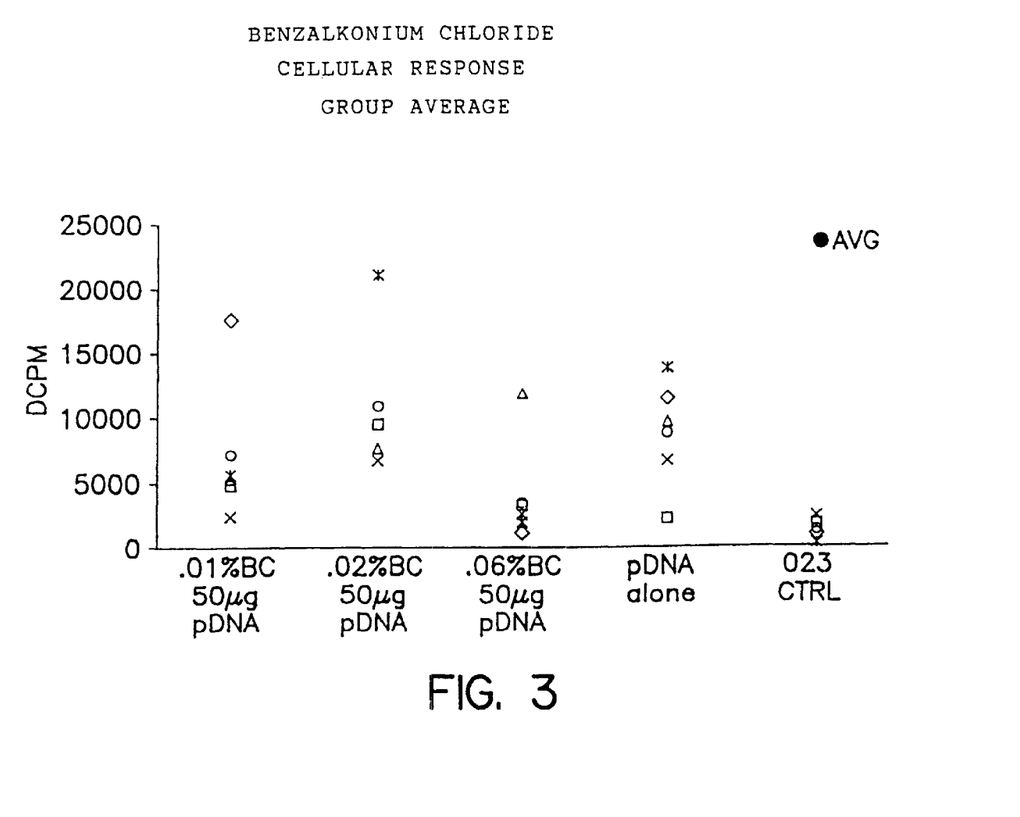
FIG. 3 is a scatter plot graph showing the individual (animals represented by ◇, □, ∆, X, and *) and group average (represented by ●) cellular responses of the animals of FIG. 1. Systemic cellular response (SI) was measured using a splenic cell proliferation assay.

The sera and spleens from each mouse and each group of mice was assayed for humoral response, i.e., antibody response to gD, as measured by a standard enzyme linked immunosorbent assay (ELISA) [J. E. Coligan et al, eds., "Current Protocols in Immunology", Vol. 1, chap. 2.1, John Wiley & Sons, Inc. (1992)]. FIGS. 1 and 2 illustrate the humoral responses of individual animals and the group average humoral responses, respectively. Antibody response calculations were conducted as follows. Based on linear regression, a linear model [O.D.=(slope×antibody concentration)+Intercept] was fitted to the standard data. The equation for the best fit.line was used to calculate antibody response for specific formulations. FIG. 3 illustrates the individual and group cellular responses of the same animals. Systemic cellular response (SI) was measured using a splenic cell proliferation assay in which was calculated the ratio of the number of spleen cells stimulated in the presence of HSV gD antigen and radiolabelled nucleotides divided by the number of the same spleen cells incubated in the absence of any antigen, but in the presence of radiolabelled nucleotides [J. E. Coligan et al, eds., "Current Protocols in Immunology", Vol. 1, chap. 2.1, John Wiley & Sons, Inc. (1992)].

FIG. 1 demonstrates that Formulation 1 (0.01% benzalkonium chloride and 0.5 mg/mL DNA) produced a significantly higher individual and group humoral response than did the positive control DNA. The group average humoral response (antibody) for Formulation 1 is 2.9 ng/mL higher than the positive control DNA alone formulation. FIG. 1 demonstrates that all five animals in Groups I and II gave humoral responses to Formulations 1 and 2, respectively; whereas only four animals in Group IV, which received the positive control DNA, produced humoral responses. The negative control DNA gave no response, as predictable. Thus, greater consistency and predictability of immune responses was seen with formulations of this invention than with DNA delivered in the absence of a transfection facilitating agent of this invention. Formulation 3 in the preparation used in this experiment produced an undesirable precipitate.

FIG. 3 demonstrates that the cellular responses for Formulations 1 and 2 (Groups I and II, respectively) are comparable to those elicited by administration of positive control DNA only (Group IV). However, again, variation in the cellular responses to formulations of this invention is minimal, compared to the wide variation in responses observed for those animals in Group IV that received DNA alone.

Based on the humoral and cellular responses in animals, as described above, it appears that benzalkonium chloride/DNA complex formulations (Formulations 1 and 2) provide better immune responses compared to DNA alone and facilitates the transfer of DNA into the subject.

EXAMPLE 5

Benzethonium Chloride:DNA Complexes

Compositions according to the present invention were also prepared using another exemplary benzylammonium-containing surfactant as described here, i.e., benzethonium chloride. These formulations were prepared in substantially the same manner as described for the benzalkonium chloride formulations of Example 4 above. The different formulations appear in Table 3 below.

TABLE 3

| Components | Formulation 1 | Formulation 2 | Formulation 3 |
|---|---|---|---|
| Plasmid DNA (mg/mL) | 0.1 | 0.5 | 0.5 |
| Benzethonium chloride (w/v) | 0.01% | 0.01% | 0.02% |
| Sucrose (w/v) | 8.71% | 8.71% | 8.71% |
| Phosphate buffer (mM) | 5 | 5 | 5 |
| pH | 6.7 ± 0.5 | 6.7 ± 0.5 | 6.7 ± 0.5 |

TEM and SEM analyses of these compositions were performed as described in Example 3. Based on TEM and SEM analysis, the structures have the same description as found for the benzalkonium chloride:DNA vesicular complexes of Example 3, i.e. uniformly sized vesicular complexes which packaged DNA.

All above-noted published references, and the provisional U.S. patent application No. 60/063,360, are incorporated herein by reference. Numerous modifications and variations of the present invention are included in the above-identified specification and are expected to be obvious to one of skill in the art. Such modifications and alterations to the compositions and processes of the present invention are believed to be encompassed in the scope of the claims appended hereto.

What is claimed is:

1. A soluble ionic complex consisting essentially of an aqueous mixture of (a) a benzylammonium group-containing surfactant of the formula:

wherein X is an anion;
each $R^1$ is independently selected from the group consisting of a hydrogen and a lower alkyl group comprising from 1 to 6 carbon atoms;
$R^2$ is selected from the group consisting of $CH_2$ and —O—;
$R^3$ is selected from the group consisting of H, $CH_3$, $C_2H_5$, phenyl, mono-substituted phenyl, and di-substituted phenyl, wherein said substitutions are independently selected from the group consisting of $C_1$–$C_{10}$ branched or straight chain alkyl groups;
n is an integer of 2 through 7, provided that when n is 1, $R^3$ is methyl, ethyl, phenyl or substituted phenyl; when n is 4 through 6, $R^3$ is H, methyl, ethyl or phenyl; when n is 6, $R^3$ is H, methyl or ethyl; and when n is 7, $R^3$ is H or methyl; and
(b) a polynucleic acid sequence.

2. The complex according to claim 1, wherein X is selected from the group consisting of halide, sulfate, and carbonate.

3. The complex according to claim 2, wherein said benzylammonium group-containing surfactant is a benzalkonium halide.

4. The complex according to claim 3 wherein said halide is chloride and said surfactant is benzalkonium chloride.

5. The complex according to claim 1, wherein said surfactant is a benzethonium halide.

6. The complex according to claim 5, wherein said surfactant is benzethonium chloride.

7. The complex according to claim 1, wherein said benzylammonium containing surfactant is present in a concentration of about 0.001 to about 2.4% w/v.

8. The complex according to claim 7, wherein said benzylammonium containing surfactant is present in a concentration of about 0.001 to about 0.1% w/v.

9. The complex according to claim 8, wherein said benzylammonium containing surfactant is present in a concentration of about 0.005 to about 0.06% w/v.

10. The complex according to claim 9, wherein said benzylammonium containing surfactant is present in a concentration of about 0.005 to about 0.03% w/v.

11. The complex according to claim 1, wherein said polynucleic acid sequence is a ribonucleic acid sequence.

12. The complex according to claim 1, wherein said polynucleic acid sequence is a deoxyribonucleic acid sequence.

13. The complex according to claim 12, wherein said deoxyribonucleic acid sequence is a plasmid.

14. The complex according to claim 1, wherein said polynucleic acid sequence is a deoxyribonucleic acid sequence.

15. The complex according to claim 12, wherein said sequence encodes a protein or a peptide.

16. The complex according to claim 1, wherein said polynucleic acid sequence is present in said complex in a concentration of between about 10 μg/ml to about 20 mg/ml.

17. The complex according to claim 16, wherein said polynucleic acid sequence is present in said complex in a concentration of between about 50 μg/ml to about 10 mg/ml.

18. The complex according to claim 17, wherein said polynucleic acid sequence is present in said complex in a concentration of between about 100 μg/ml to about 1.0 mg/ml.

19. A composition consisting essentially of the complex according to claim 1 and additives selected from the group consisting of buffering agents and tonicity adjusting agents.

20. The composition according to claim 19, which is an injectable formulation.

21. A method of inducing an immune response in a mammalian subject to a viral, prokaryotic or eukaryotic pathogenic antigen comprising the step of administering by injection to cells of said subject, an effective amount of the complextion of claim 19, wherein said polynucleic acid sequence comprises a sequence which encodes at least one epitope that is identical or substantially similar to an epitope of the pathogenic antigen, said epitope-encoding sequence under the control of regulatory sequences that direct expression of said protein in the cells of said subject.

22. The method according to claim 21, wherein composition is administered by an injection route selected from the group consisting of intramuscularly, intraperitoneally, intradermally, subcutaneously, intravenously, intraarterially, and intraoccularly.

23. The complex according to claim 1, wherein said surfactant is benzalkonium chloride, said polynucleic acid is plasmid DNA, and said aqueous mixture is an isotonic solution.

24. A method of immunizing a mammalian subject against a pathogen comprising the step of administering by injection to said subject an effective amount of the composition of claim 19, wherein said polynucleic acid sequence comprises a nucleotide sequence encoding at least one protein epitope that is identical to an antigen of the pathogen, said protein epitope encoding sequence is operatively linked to regulating sequences directing the expression of said protein epitope in the cells of said subject.

25. The method according to claim 24, wherein said polynucleic acid sequence is administered by an injection route selected from the group consisting of intramuscularly, intraperitoneally, intradermally, subcutaneously, intravenously, intraarterially, and intraoccularly.

26. A composition consisting essentially of a polynucleic acid sequence substantially packaged in a vesicular complex formed by an aqueous mixture of a benzylammonium-containing surfactant of the formula:

wherein X is an anion;
each $R^1$ is independently selected from the group consisting of a hydrogen and a lower alkyl group comprising from 1 to 6 carbon atoms;
$R^2$ is selected from the group consisting of $CH_2$ and —O—;
$R^3$ is selected from the group consisting of H, $CH_3$, $C_2H_5$, phenyl, mono-substituted phenyl, and di-substituted phenyl, wherein said substitutions are independently selected from the group consisting of $C_1$–$C_{10}$ branched or straight chain alkyl groups;
n is an integer of 2 through 7, provided that when n is 1, $R^3$ is methyl, ethyl, phenyl or substituted phenyl; when n is 4 through 6, $R^3$ is H, methyl, ethyl or phenyl; when n is 6, $R^3$ is H, methyl or ethyl; and when n is 7, $R^3$ is H or methyl;
and said polynucleic acid sequence.

27. A composition consisting essentially of multiple vesicular complexes of uniform size, each of said vesicular complexes consisting essentially of a polynucleic acid sequence substantially packaged in a vesicular complex formed by an aqueous mixture of a benzylammonium-containing surfactant of the formula:

wherein X is an anion;
each $R^1$ is independently selected from the group consisting of a hydrogen and a lower alkyl group comprising from 1 to 6 carbon atoms;
$R^2$ is selected from the group consisting of $CH_2$ and —O—;
$R^3$ is selected from the group consisting of H, $CH_3$, $C_2H_5$, phenyl, mono-substituted phenyl, and di-substituted phenyl, wherein said substitutions are independently selected from the group consisting of $C_1$–$C_{10}$ branched or straight chain alkyl groups;
n is an integer of 2 through 7, provided that when n is 1, $R^3$ is methyl, ethyl, phenyl or substituted phenyl; when n is 4 through 6, $R^3$ is H, methyl, ethyl or phenyl; when n is 6, $R^3$ is H, methyl or ethyl; and when n is 7, $R^3$ is H or methyl;
and said polynucleic acid sequence.

28. The composition according to claim 27 formed by mixing an aqueous solution of the surfactant with a polynucleic acid sequence.

29. A method of introducing a polynucleic acid sequence into a cell comprising the step of contacting said cell with a member of the group consisting of:
(a) the complex of claim 1;
(b) the composition of claim 26; and
(C) the composition of claim 27.

30. A pharmaceutical composition selected from the group consisting of:
(a) a composition consisting essentially of a polynucleic acid sequence substantially packaged in a vesicular complex formed by an aqueous mixture of a benzylammonium-containing surfactant of the formula:

wherein X is an anion;
each $R^1$ is independently selected from the group consisting of a hydrogen and a lower alkyl group comprising from 1 to 6 carbon atoms;
$R^2$ is selected from the group consisting of $CH_2$ and —O—;
$R^3$ is selected from the group consisting of H, $CH_3$, $C_2H_5$, phenyl, mono-substituted phenyl, and di-substituted phenyl, wherein said substitutions are independently selected from the group consisting of $C_1$–$C_{10}$ branched or straight chain alkyl groups;
n is an integer of 2 through 7, provided that when n is 1, $R^3$ is methyl, ethyl, phenyl or substituted phenyl; when n is 4 through 6, $R^3$ is H, methyl, ethyl or phenyl; when n is 6, $R^3$ is H, methyl or ethyl; and when n is 7, $R^3$ is H or methyl; and said polynucleic acid sequence; and (b) a composition consisting essentially of multiple vesicular complexes of uniform size, each of said vesicular complexes consisting essentially of a polynucleic acid sequence substantially packaged in a vesicular complex formed by an aqueous mixture of a benzylammonium-containing surfactant of the formula:

wherein X is an anion;
each $R^1$ is independently selected from the group consisting of a hydrogen and a lower alkyl group comprising from 1 to 6 carbon atoms;
$R^2$ is selected from the group consisting of $CH_2$ and —O—;
$R^3$ is selected from the group consisting of H, $CH_3$, $C_2H_5$, phenyl, mono-substituted phenyl, and di-substituted phenyl, wherein said substitutions are independently selected from the group consisting of $C_1$–$C_{10}$ branched or straight chain alkyl groups;
n is an integer of 2 through 7, provided that when n is 1, $R^3$ is methyl, ethyl, phenyl or substituted phenyl; when n is 4 through 6, $R^3$ is H, methyl, ethyl or phenyl; when n is 6, $R^3$ is H, methyl or ethyl; and when n is 7, $R^3$ is H or methyl; and said polynucleic acid sequence.

31. A method of facilitating the uptake of a polynucleic acid sequence into a cell comprising contacting said cell with a soluble ionic complex consisting essentially of an aqueous mixture of
(a) a benzylammonium group-containing surfactant of the formula:

wherein X is an anion;
each $R^1$ is independently selected from the group consisting of a hydrogen and a lower alkyl group comprising from 1 to 6 carbon atoms;
$R^2$ is selected from the group consisting of $CH_2$ and —O—;
$R^3$ is selected from the group consisting of H, $CH_3$, $C_2H_5$, phenyl, mono-substituted phenyl, and di-substituted phenyl, wherein said substitutions are independently selected from the group consisting of $C_1$–$C_{10}$ branched or straight chain alkyl groups;
n is an integer of 2 through 7, provided that when n is 1, $R^3$ is methyl, ethyl, phenyl or substituted phenyl; when n is 4 through 6, $R^3$ is H, methyl, ethyl or phenyl; when n is 6, $R^3$ is H, methyl or ethyl; and when n is 7, $R^3$ is H or methyl; and
(b) a polynucleic acid sequence.

32. The method according to claim 31, wherein said complex is in the form of a vesicular complex in which the polynucleic acid sequence is substantially packaged.

33. The complex according to claim 1, which forms a vesicular complex in which the polynucleic acid sequence is substantially packaged.

* * * * *